United States Patent [19]

Shin

[11] Patent Number: 4,603,221

[45] Date of Patent: Jul. 29, 1986

[54] PROCESS FOR PREPARING SUBSTITUTED TETRALONES

[75] Inventor: Kju H. Shin, Baton Rouge, La.

[73] Assignee: Ethyl Corporation, Richmond, Va.

[21] Appl. No.: 742,881

[22] Filed: Jun. 10, 1985

[51] Int. Cl.$^4$ ............................................. C07C 45/28
[52] U.S. Cl. ................................................... 568/309
[58] Field of Search ........................................ 568/309

[56] References Cited

U.S. PATENT DOCUMENTS 3,873,580   3/1975   Rennie ................................. 568/309
4,146,582   3/1979   Maggioni ............................. 568/309

OTHER PUBLICATIONS

Stork, J.A.C.S., vol. 69, pp. 576–579 (1947).
Thomas et al, J.A.C.S., vol. 70, pp. 331–334 (1948).
Bhatt et al., Tet Letters, vol. 22, pp. 2605–2608 (1981).
Gero et al, J. Org. Chem., vol. 16, pp. 1835–1838 (1951).

*Primary Examiner*—James H. Reamer
*Attorney, Agent, or Firm*—Donald L. Johnson; John F. Sieberth; Patricia J. Hogan

[57] ABSTRACT

6-Alkoxytetralones are prepared by gradually adding a persulfate to a heated mixture of a 6-alkoxytetralin, a salt of a divalent metal, and a tertiary amine and maintaining the 6-alkoxytetralin in intimate admixture with the persulfate until it has been oxidized to the corresponding 6-alkoxytetralone. The reaction is preferably conducted in solution or dispersion. Preferred reaction ingredients are 6-methoxytetralin, cupric sulfate, an alkylpyridine, and sodium persulfate.

20 Claims, No Drawings

PROCESS FOR PREPARING SUBSTITUTED TETRALONES

FIELD OF INVENTION

This invention relates to 6-alkoxytetralones and more particularly to a process for preparing them.

BACKGROUND

It is known that 6-alkoxytetralones are useful as chemical intermediates, especially as pharmaceutical intermediates, and that they can be prepared in various ways. As taught by Stork, *Journal of the American Chemical Society*, Vol. 69, pp. 576–579 (1947), Thomas et al., *Journal of the American Chemical Society*, Vol. 70, pp. 331–334 (1948), and Bhatt et al., *Tetrahedron Letters*, Vol. 22, pp. 2605–2608 (1981), the 6-alkoxytetralones can be prepared by the oxidation of 6-alkoxytetralins, but these known oxidation techniques have not proved to be commercially attractive.

SUMMARY OF INVENTION

An object of this invention is to provide a novel process for preparing 6-alkoxytetralones.

Another object is to provide such a process wherein the 6-alkoxytetralones are prepared from 6-alkoxytetralins.

A further object is to provide such a process which is commercially attractive.

These and other objects are attained by heating a mixture of a 6-alkoxytetralin, a salt of a divalent metal, and a tertiary amine to a temperature not higher than about 100° C., gradually adding a persulfate to the reaction mixture, and maintaining the 6-alkoxytetralin in intimate admixture with the persulfate so as to oxidize it to a 6-alkoxytetralone.

DETAILED DESCRIPTION

The 6-alkoxytetralin that is oxidized in the process of the invention may be any 6-alkoxytetralin but is generally a 6-alkoxytetralin wherein the alkoxy group contains 1–20, preferably 1–6 carbons, such as the 6-alkoxytetralins wherein the alkoxy group is methoxy, ethoxy, 1-methylethoxy, butoxy, hexoxy, etc. A particularly preferred 6-alkoxytetralin is 6-methoxytetralin.

As indicated in Stork, Thomas et al., and the references cited therein, all of which are incorporated herein by reference, these compounds, when not commercially available, can be prepared by the catalyst hydrogenation of the appropriate 6-alkoxynaphthalene, by the sulfonation, alkali fusion, and alkylation of tetralin, or by the catalytic hydrogenation of the appropriate 7-alkoxytetralone. However, when it is necessary to synthesize the 6-alkoxytetralin, the synthesis is most conveniently accomplished by reacting 6-hydroxytetralin with sodium hydroxide and then with a suitable alkylating agent, such as the appropriate alkyl halide or dialkyl sulfate.

The salt employed in the process of the invention is a catalyst and may be a salt of any divalent metal, i.e., a metal which has two valence states and is in the bivalent state in the sulfate. Thus, e.g., it may be a sulfate, nitrate, or halide of titanium, vanadium, chromium, manganese, iron, cobalt, nickel, or copper, but it is preferably cupric or ferrous sulfate, most preferably cupric sulfate. The amount of salt employed is generally in the range of about 0.1–1.2 mols, preferably about one mol, per mol of 6-alkoxytetralin.

The tertiary amine used in the process is an ingredient that improves the yield of product, its efficacy generally increasing with increased basicity. Thus, it is preferably a tertiary amine having a pKa value of at least about 5.23, most preferably at least about 6.62 as determined by a method generally in accordance with the method taught in Gero et al., *Journal of Organic Chemistry*, vol. 16, pp. 1835–1838 (1951), the teachings of which are incorporated herein by reference. Exemplary of such amines are trialkylamines, such as trimethyl, triethyl, tripropyl, etc., amines; pyridines, such as pyridine, the 2- and 4-methylpyridines, the 2,4- and 2,6-dimethylpyridines, 2,4,6-trimethylpyridine, the corresponding alkylpyridines wherein the alkyl groups are ethyl, propyl, etc., 2-methyl-5-ethylpyridine, etc. The preferred tertiary amines are pyridines, especially alkylpyridines, and most especially alkylpyridines having a pKa value of at least about 6.62. This yield improver is typically employed so as to provide about 0.5–6, preferably about 2–5, mols of amine per mol of 6-alkoxytetralin.

As indicated above, the oxidizing agent of the process is a persulfate, and it may be any compound capable of generating persulfate ion, e.g., ammonium persulfate or any alkali metl persulfate. However, as a practical matter, it is preferred to use sodium, potassium, or ammonium persulfate; and sodium persulfate is particularly preferred. The amount of persulfate employed is usually about 2–4 mols per mol of 6-alkoxytetralin.

In the practice of the invention, the 6-alkoxytetralin, salt, and tertiary amine are mixed with one another and brought to the desired reaction temperature prior to the addition of the persulfate. This reaction temperature can be any temperature between about room temperature and about 100° C., but it is preferably in the range of about 65°–70° C. because of the higher yields obtained at such reaction temperatures. After the reaction temperature has been achieved, the persulfate is gradually added to the other ingredients so as to achieve an intimate admixture and permit the attainment of higher product yields than can be obtained when the reaction ingredients are brought together more abruptly, e.g., as in Bhatt et al. The achievement of an intimate admixture is facilitated by the use of stirring, and it is also efficacious to solubilize or disperse the reaction ingredients in suitable media prior to the addition of the persulfate.

When solubilization or dispersion of the reaction ingredients is desired, it is generally achieved by dissolving or dispersing the 6-alkoxytetralin, salt, and tertiary amine in a suitable inert organic solvent, such as acetonitrile, propionitrile, acetone, methanol or other lower alcohol, etc., and/or dissolving the persulfate in water. It is most efficacious to dissolve or disperse both sets of ingredients. However, it has been found that the gradual addition of solid persulfate to a solution or dispersion of the other ingredients or the gradual addition of an aqueous solution of persulfate to a reaction mixture consisting only of the 6-alkoxytetralin, the salt, and the tertiary amine has advantages over a neat reaction even if not as much of an advantage as the use of solutions or dispersions of both sets of ingredients.

After the persulfate has been added, it is maintained in intimate admixture with the 6-alkoxytetralin for a suitable time, e.g., about 1–5 hours when the preferred temperatures are used, to oxidize the tetralin to the corresponding tetralone. The 6-alkoxytetralone can then be recovered by conventional techniques.

The invention is advantageous in that it provides a commercially attractive process capable of producing 6-alkoxytetralones in high yields. It also has the advantage of permitting the use of crude 6-alkoxytetralins containing the 3-alkoxytetralins which are formed as by-products in the 6-alkoxytetralin synthesis and which are difficult to separate therefrom. When such a crude 6-alkoxytetralin is employed in the process of the invention, the 3-alkoxytetralin impurity is an inert ingredient and is easily separated from the 6-alkoxytetralone product by distillation.

The following examples are given to illustrate the invention and are not intended as a limitation thereof.

EXAMPLE I

A solution of 30.31 g of 85% pure 6-methoxytetralin containing 15% of 3-methoxytetralin (158.8 mmols of 6-isomer), 22.4 g (140.4 mmols) of cupric sulfate, and 88.2 g (728.1 mmols) of 2-methyl-5-ethylpyridine in 150 ml of acetonitrile was heated to 60° C. with stirring under nitrogen. A solution of 106.8 g (448.7 mmols) of sodium persulfate in 163 ml of water was added dropwise over a period of 80 minutes at 65°–69° C., after which the reaction was continued at that temperature for another hour. The reaction mixture was then cooled to 25° C., and the solid was filtered off and rinsed three times with toluene, after which the filtrate was washed with water. HPLC analysis of the toluene layer showed that the yield of 6-methoxytetralone was 92.2%.

Toluene and acetonitrile were removed by distillation. The residue was carefully distilled in vacuo to recover 3-methoxytetralin, trace amounts of unreacted 6-methoxytetralin, and 6-methoxytetralone. The final distillate was recrystallized from n-heptane to provide a 73.4% isolated yield of 6-methoxytetralone.

EXAMPLE II

To determine the effect of the basicity of the tertiary amine on product yield, a series of reactions was conducted in which sodium persulfate was reacted with 85% pure 6-methoxytetralin at 65° C. for 1.5 hours in the presence of cupric sulfate and a base. The bases used, their pKa values, and the HPLC product yields obtained are shown below.

| Run | Base | pKa Value | Yield (%) |
|---|---|---|---|
| A | pyridine | 5.23 | 62.9 |
| B | 2,6-lutidine | 6.62 | 69.9 |
| C | 2,4-lutidine | 6.79 | 78.4 |

It is obvious that many variations can be made in the products and processes set forth above without departing from the spirit and scope of this invention.

What is claimed is:

1. A process which comprises heating a mixture of (A) a 6-alkoxytetralin, (B) a sulfate, nitrate, or halide salt of bivalent titanium, vanadium, chromium, manganese, iron, cobalt, nickel, or copper, and (C) a tertiary amine having a pKa value of at least about 5.23 to a temperature not higher than about 100° C., gradually adding an ammonium or alkali metal persulfate to the reaction mixture, and maintaining the 6-alkoxytetralin in intimate contact with the persulfate so as to oxidize it to a 6-alkoxytetralone.

2. The process of claim 1 wherein the 6-akoxytetralin is 6-methoxytetralin.

3. The process of claim 1 wherein the salt is a sulfate.

4. The process of claim 3 wherein the sulfate is cupric sulfate.

5. The process of claim 1 wherein the tertiary amine has a pKa value of at least about 6.62.

6. The process of claim 1 wherein the tertiary amine is a pyridine.

7. The process of claim 6 wherein the pyridine is an alkylpyridine.

8. The process of claim 7 wherein the alkylpyridine is 2-methyl-5-ethylpyridine.

9. The process of claim 1 wherein the persulfate is an alkali metal or ammonium persulfate.

10. The process of claim 9 wherein the persulfate is sodium persulfate.

11. The process of claim 1 wherein the reaction mixture contains about 0.1–1.2 mols of salt, about 0.5–6 mols of tertiary amine, and about 2–4 mols of persulfate per mol of 6-alkoxytetralin.

12. The process of claim 11 wherein the reaction mixture contains about one mol of salt, about 2–5 mols of tertiary amine, and about 2–4 mols of persulfate per mol of 6-alkoxytetralin.

13. The process of claim 1 wherein the mixture of 6-alkoxytetralin, salt, and tertiary amine is a solution in an inert organic solvent.

14. The process of claim 13 wherein the solvent is acetonitrile.

15. The process of claim 1 wherein the persulfate is added to the reaction mixture as an aqueous solution.

16. The process of claim 1 wherein the reaction is conducted at a temperature in the range of about 65°–70° C.

17. A process which comprises heating a mixture of one molar proportion of 6-methoxytetralin, about 0.1–1.2 molar proportions of cupric sulfate, and about 0.5–6 molar proportions of an alkylpyridine in acetonitrile to a temperature of about 65°–70° C., gradually adding an aqueous solution of about 2–4 molar proportions of sodium persulfate to the reaction mixture, and maintaining the 6-methoxytetralin in intimate admixture with the persulfate so as to oxidize it to 6-methoxytetralone.

18. The process of claim 17 wherein the reaction mixture contains about 2–5 molar proportions of the alkylpyridine.

19. The process of claim 18 wherein the reaction mixture contains about one molar proportion of cupric sulfate.

20. The process of claim 1 wherein the reaction mixture contains about 2–5 mols of tertiary amine per mol of 6-alkoxytetralin.

* * * * *